United States Patent [19] [11] 4,343,806
Harbridge [45] Aug. 10, 1982

[54] BENZYLAMINO CLAVULANATES AND THEIR PRODUCTION

[75] Inventor: John B. Harbridge, Coulsdon, England

[73] Assignee: Beecham Group Limited, England

[21] Appl. No.: 83,838

[22] Filed: Oct. 11, 1979

[30] Foreign Application Priority Data

Oct. 25, 1978 [GB] United Kingdom ............... 41957/78

[51] Int. Cl.³ .................... C07D 498/04; A61K 31/42
[52] U.S. Cl. .................................... 424/272; 542/420; 260/245.3
[58] Field of Search ..................... 542/420; 260/245.3; 424/272

[56] References Cited
FOREIGN PATENT DOCUMENTS
79494 4/1978 Belgium .
2646003 4/1977 Fed. Rep. of Germany .

OTHER PUBLICATIONS
Stirling et al., Chem. Abs. 90, 168574x, (1978).

Primary Examiner—Mark L. Berch
Attorney, Agent, or Firm—Jacobs & Jacobs

[57] ABSTRACT

The compounds of the formula (II):

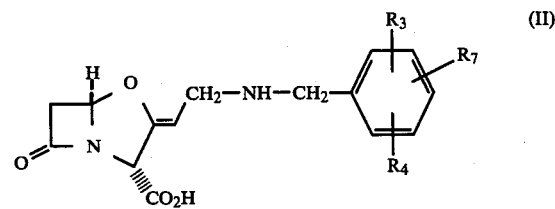

wherein $R_3$ and $R_4$ are as defined in relation to formula (I) and $R_7$ is a nitro, cyano, amino or aminomethyl group, are antibacterial agents and β-lactamase inhibitors. Their use and a process for their preparation are described.

76 Claims, No Drawings

BENZYLAMINO CLAVULANATES AND THEIR PRODUCTION

West Germany Offenlegunsschrift No. 2817085 discloses inter alia the compounds of the formula (I):

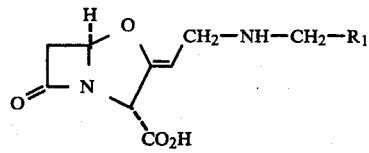

or an ester thereof wherein $R_1$ is a hydrogen atom, an alkyl group of up to 5 carbon atoms, a cycloalkyl group of 5 or 6 carbon atoms, a hydroxyalkyl group of up to 5 carbon atoms or a moiety of the sub-formula (a):

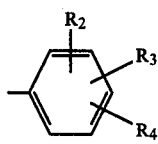

wherein $R_2$ is a hydrogen, fluorine, chlorine or bromine, atom or an alkyl group of 1-3 carbon atoms, an alkoxyl group of 1-3 carbon atoms, an acyloxyl group of 1-3 carbon atoms, a hydroxyl group, an alkoxycarbonyl group containing 1-3 carbon atoms in the alkoxy part, or a group $-N(R_5)CO.R_6$, $-N(R_5)SO_2R_6$ or $-CO-NR_5R_6$ where $R_5$ is a hydrogen atom or an alkyl group of 1-3 carbon atoms or a phenyl or benzyl group and $R_6$ is an alkyl group of 1-3 carbon atoms or a phenyl or benzyl group; $R_3$ is a hydrogen fluorine or chlorine atom or an alkyl group of 1-3 carbon atoms, an alkoxyl group of 1-3 carbon atoms or an acyloxyl group of 1-3 carbon atoms; and $R_4$ is a hydrogen fluorine or chlorine atom or an alkyl group of 1-3 carbon atoms or an alkoxyl group of 1-3 carbon atoms.

Nowhere in the said Offenlegunsschrift was it suggested that nitrobenzyl or aminobenzyl groups could advantageously form part of the molecule. Compounds of this type have now been prepared and have been found to possess useful β-lactamase inhibitory and antibacterial activity.

The present invention provides the compounds of the formula (II):

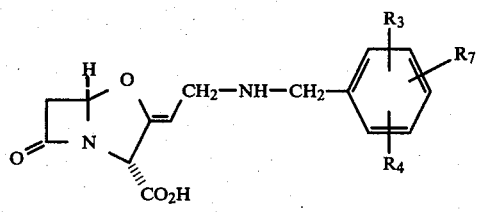

wherein $R_3$ and $R_4$ are as defined in relation to formula (I) and $R_7$ is a nitro, cyano, amino or aminomethyl group.

Since the compounds of the formula (II) exist as zwitterions they may also be represented by the formulae (III), (IV), (V) and (VI):

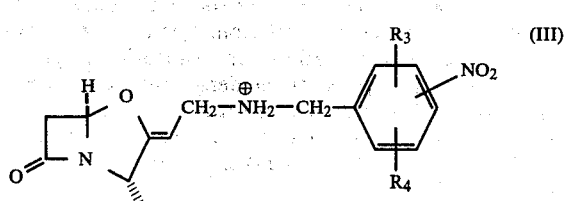

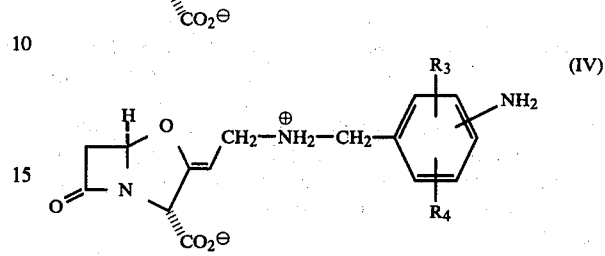

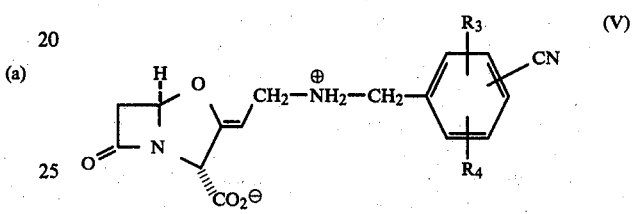

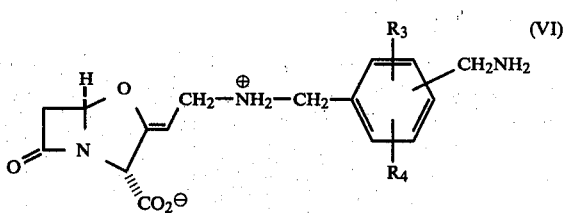

wherein $R_3$ and $R_4$ are as defined in relation to formula (II).

More suitably $R_3$ is a hydrogen, fluorine or chlorine atom or a methoxyl, ethoxyl, acetoxyl, propionoxyl, methyl or ethyl group.

More suitably $R_4$ is a hydrogen, fluorine or chlorine atom or a methoxyl, ethoxyl, acetoxyl, propionoxyl, methyl or ethyl group.

Most suitably $R_3$ is a hydrogen, fluorine or chlorine atom or a methoxyl or methyl group.

Most suitably $R_4$ is a hydrogen atom or a methyl or methoxyl group.

Preferably $R_3$ is a hydrogen atom.

Preferably $R_4$ is a hydrogen atom.

The amino group present in the compounds of the formulae (IV) and (VI) may be salted if desired, for example, it may be in the form of an acid-addition salt with a pharmaceutically acceptable acid such as hydrochloric acid. However, this is not usually preferred, for the compound of the formula (IV).

Aptly the compound of this invention is of the formulae (III) or (V). Aptly the compound of this invention is of the formulae (III) or (IV).

The present invention also provides a pharmaceutical composition which comprises a compound of this invention and a pharmaceutically acceptable carrier.

The compositions of the invention include those in a form adapted for oral, topical or parenteral use and may be used for the treatment of the infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

Compounds of this invention when in highly pure crystalline form tend to have relatively low aqueous solubilities so that if it is desired to administer substantial quantities of the medicament this can require fairly large quantities of water for reconstitution. In these circumstances it is often convenient to administer the solution intravenously.

An alternative approach to administering the compounds of this invention is to utilise an injectable suspension. Such suspensions may be made up in sterile water, sterile saline or the like and may also contain suspending agents such as polyvinylpyrrolidone, lecithin or the like (for example in the manner described for amoxycillin trihydrate in Belgian Pat. No. 839109). Alternatively such compositions may be prepared in an acceptable oily suspending agent such as arachis oil or its equivalent.

Unit dose compositions comprising a compound of this invention adapted for oral administration form a further suitable composition aspect of this invention. Orally administrable compositions are of use as synergistically effective blood levels can be expected at high doses and at lower doses such compositions may be used to treat infections localised in the gastro-intestinal tract.

Unit dose compositions comprising a compound of this invention adapted for topical administration are also presented by this invention. In this instance "topical administration" also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or a cephalosporin. Considerable advantages accrue from the inclusion of a penicillin or cephalosporin since the resulting composition shows enhanced effectiveness (synergy).

Penicillins suitable for inclusion in orally administrable compositions of this invention include benzylpenicillin, phenoxymethylpenicillin, propicillin, amoxycillin, ampicillin, epicillin, cyclacillin and other orally active penicillins and their pharmaceutically acceptable salts and in-vivo hydrolysable esters and aldehyde and ketone adducts of those penicillins containing a 6-α-aminoacylamino side chain and their pharmaceutically acceptable salts. Suitable penicillin in-vivo hydrolysable esters include the acetoxymethyl, pivaloyloxymethyl, α-ethoxycarbonyloxyethyl and phthalidyl esters of ampicillin or amoxycillin or the phenyl, tolyl and indanyl α-esters of carbenicillin and ticarcillin and pharmaceutically acceptable salts thereof. Suitable aldehyde and ketone adducts of penicillins containing a 6-α-aminoacylamino side chain include the formaldehyde and acetone adducts of ampicillin and amoxycillin such as metampicillin and hetacillin and their salts. Suitable penicillins for inclusion in injectably or infusably administrable compositions include the pharmaceutically acceptable salts of benzylpenicillin, phenoxymethylpenicillin, carbenicillin, propicillin, ampicillin, amoxycillin, epicillin, ticarcillin and cyclacillin.

Cephalosporins suitable for inclusion in orally administrable compositions of this invention include cephalexin, cephradine, cephaloglycine their pharmaceutically acceptable salts and other known cephalosporins and their pharmaceutically acceptable salts and in-vivo hydrolysable esters and aldehyde and ketone adducts of those cephalosporins containing a 7-α-aminoacylamino side chain and their pharmaceutically acceptable salts. Suitable cephalosporins for inclusion in the injectable or infusable compositions of this invention include the pharmaceutically acceptable salts of cephaloridine, cephalothin, cefazolin, cephalexin, cephacetrile, cephamandole, cephapirin, cephradine, cephaloglycine and other known cephalosporins.

When present in a pharmaceutical composition together with a penicillin or cephalosporin, the weight ratio of synergist or its salt present to penicillin or cephalosporin present may be from, for example 3:1 to 1:10 for example 1:1 to 1:4.

Suitably the weight of the compound of this invention in a unit dosage form of this invention will be from 50 to 500 mg and more suitably from 50 to 250 mg.

In general the total quantity of antibacterial agents present in a synergistic composition of this invention will not be greater than 1500 mg and will usually be between 100 and 1000 mg.

Normally between 500 and 3000 mg of the synergistic compositions of the invention will be administered each day of treatment (to an average 70 kg adult). However, for the treatment of severe systemic infections or infections of particularly intransigent organisms, higher doses may be used in accordance with clinical practice.

One particularly favoured composition of this invention will contain from 150 to 1000 mg of amoxycillin as the trihydrate or sodium salt and from 25 to 500 mg of a compound of this invention.

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillin hydrochloride, bacampicillin hydrochloride or talampicillin hydrochloride.

Most suitably the preceding compositions will contain from 200 to 700 mg of the penicillin component. Most suitably the preceding composition will comprise from 50 to 250 mg of a compound of the formula (III) to (VI) in crystalline form.

Another particularly favoured composition of this invention will contain from 200 to 2000 mg of carbenicillin, ticarcillin or a pro-drug therefor and from 50 to 500 mg of a compound of the invention.

Suitably this form of composition will contain disodium carbenicillin. Suitably this form of the composition will contain di-sodium ticarcillin.

More suitably this form of the composition will contain from 75 to 250 mg of a compound of the formula (III) to (VI) in crystalline form.

The present invention also provides a method of treating bacterial infections in humans or domestic mammals which comprises the administration of a composition of this invention.

Commonly the infection treated will be due to a strain of *Staphylococcus aureus, Klebsiella aerogenes, Escherichia coli,* Proteus sp. or the like. The organisms believed to be most readily treated by an antibacterially effective amount of a compound of this invention are strains of *Staphylococcus aureus*. The other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

The present invention also provides a process for the preparation of a compound the formula (II) as hereinbefore defined which process comprises the catalytic hydrogenation of a compound of the formula (VII):

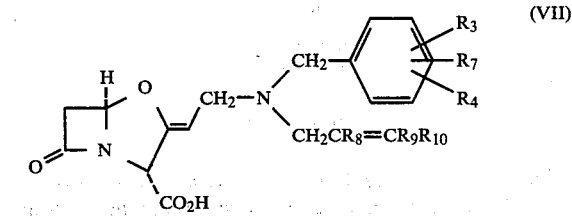

(VII)

or a hydrogenolysable ester thereof wherein $R_3$, $R_4$ and $R_7$ are as defined in relation to formula (II) or are moieties $R_3^1$, $R_4^1$, $R_7^1$ that on hydrogenation provide groups $R_3$, $R_4$ and $R_7$ as defined in relation to formula (II), $R_8$ is a lower alkyl group or a hydrogen atom, $R_9$ is a hydrogen atom or a lower alkyl group and $R_{10}$ is a hydrogen atom or a lower alkyl or phenyl group, or when $R_9$ is a hydrogen atom $R_8$ and $R_{10}$ together may represent a butadiene moiety.

When used herein the term "hydrogenolysable ester" means an ester which on hydrogenation is cleaved to yield the parent carboxylic acid.

When used herein the term "lower alkyl" means an alkyl group of up to 4 carbon atoms.

Particularly apt groups $CH_2CR_8=CR_9R_{10}$ for use in the compounds of the formula (VII) include the following: $CH_2C(CH_3)=CH_2$, $CH_2C(C_2H_5)=CH_2$, $CH_2(n.C_3H_7)=CH_2$, $CH_2C(CH_3)=CH.CH_3$, $CH_2C(CH_3)=C(CH_3)_2$, $CH_2C(CH_3)=CH.C_2H_5$ and $CH_2C(CH_3)=CH.C_6H_5$.

A favoured group $CH_2CR_8=CR_9R_{10}$ is the $CH_2C(CH_3)=CH_2$ group.

A further favoured group $CH_2CR_8=CR_9R_{10}$ is the $CH_2C(CH_3)=CHC_6H_5$ group.

Non-limiting examples of moieties $R_3^1$, $R_4^1$ and $R_7^1$ that on hydrogenation provide groups $R_3$, $R_4$ and $R_7$ as hereinbefore defined are the benzyloxycarbonyloxy group which affords a hydroxyl group and the benzyloxycarbonylamino group which affords an amino group.

The compound of the formula (VII) may be preformed although it is normally produced in situ by hydrogenation of a hydrogenolysable ester. It follows that it is a preferred form of the process of this invention to employ a hydrogenolysable ester of a compound of the formula (VII).

Hydrogenolysable esters for use in this invention are generally benzyl or substituted benzyl esters: and also optionally substituted allyl esters. Suitable esters include those of the part-formula (b); $CO_2CHA_1A_2$ wherein $A_1$ is a hydrogen atom or a lower alkyl or optionally substituted phenyl group and $A_2$ is an optionally substituted phenyl group.

Favourably $A_1$ is a hydrogen atom.

The nature of the substituent employed in a substituted phenyl group is unimportant as long as it does not interfere with the hydrogenolytic cleavage. Thus suitable substituents include lower alkyl, lower alkoxyl, lower acyloxyl, lower acyl, nitro, cyano, carboxylic acid groups or salts or lower alkyl esters or amides thereof, nitro, halo or similar substituents. Apt substituents include methyl, methoxyl, nitro, chloro, bromo and the like. One, two or three such substituents may be employed (except not more than one nitro group should be present).

Favoured esters include the benzyl, nitrobenzyl, bromobenzyl, chlorobenzyl, methylbenzyl and methoxybenzyl esters. Particularly favoured esters include the benzyl, p-nitrobenzyl and p-methoxybenzyl esters. The preferred ester is the benzyl ester.

Further preferred hydrogenolysable ester groups include those groups $CH_2CR_8=CR_9R_{10}$ that have been specified hereinbefore as being favoured for removal from a nitrogen atom by hydrogenolysis.

The hydrogenation reaction is normally carried out in the present of a transition metal catalyst.

The catalyst we have preferred to use is palladium, for example in the form of palladium on carbon (charcoal), palladium on barium sulphate, palladium on calcium carbonate, palladium black or the like.

A favoured catalyst is palladium on carbon (sometimes referred to as palladium on charcoal); for example 5%, 10%, 20% or 30% palladium on carbon.

The higher palladium content catalyst can be particularly apt as smaller total weights of catalyst can be employed thereby avoiding possible problems associated with adsorption of product onto the carbon. Alternatively use of a catalyst containing a lower proportion of metal and a higher quantity of carbon can be used specifically to adsorb the product. This aids in isolation as the product may be recovered therefrom thereafter by washing.

A low, medium or high pressure of hydrogen may be used in this reaction, for example from 1 to 6 atmospheres.

However it is one of the considerable advantages of the process of this invention that it proceeds smoothly and quickly even at atmospheric pressure. Thus a particularly favoured aspect of this invention comprises carrying out the hydrogenation at atmospheric pressure.

The reaction is normally carried out at a nonextreme temperature, for example from 0° C. to 30° C. and more usually from 12° C. to 25° C. It is generally convenient to carry out the reaction at ambient temperature.

Suitable solvents for carrying out the hydrogenation include ethanol, n-propanol, isopropanol, tetrahydrofuran, dioxan, ethyl acetate or mixtures of such solvents or such solvents in the presence of water. A favoured solvent is ethanol.

The product may generally be isolated from the reaction mixture by filtering off the solids (the catalyst, which should be well washed to remove the product) and then evaporating the solvent, preferably under low pressure, to yield the initial product. Further purification may be effected by such conventional methods as chromatography over cellulose or other mild stationary phase eluting with a $C_{1-4}$ alkanol optionally in the presence of water and optionally in the presence of tetrahydrofuran. A preferred purification method utilises a combination of ethyl acetate, isopropanol and water as the eluant over silica. A further preferred purification method utilises a combination of n-butanol, isopropanol and water as the eluant over cellulose. Evaporation of the combined active fraction (identified by aqueous potassium permanganate spray on tlc) then yields the desired compound in pure form.

The desired product is normally obtained in crystalline form (unless it is an unsalted ester). Trituration under ethanol, isopropanol or the like $C_{1-4}$ alkanol or other conventional solvent such as a ketone, ether or ester solvent or other conventional solvent (for example of up to 6 carbon atoms and more suitably of up to 4 carbon atoms) may also be used to aid crystallisation. Recrystallisation from ethanol or the like may also be employed. The solvent used in such processes may advantageously be moist.

The compounds of the formula (VII) as hereinbefore defined and their hydrogenolysable esters are useful intermediates and as such form part of this invention.

The compounds of the formula (VII) and their hydrogenolysable esters may be prepared by the methods set forth in U.S. Ser. No. 731,928, abandoned.

The present invention also provides a process for the preparation of a compound of the formula (II) which process comprises the reduction with a water soluble complex hydride of a salt of a compound of the formula (VIII):

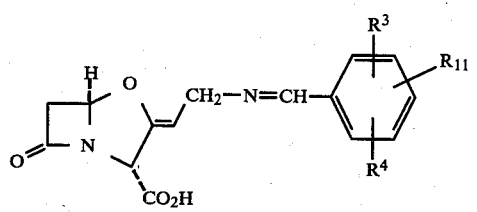

wherein $R^3$ and $R^4$ are as defined in relation to formula (II) and $R_{11}$ is a $NO_2$ or CN group and thereafter if desired reducing the $NO_2$ or CN group to an amino or aminomethyl group and if desired salifying the amino group thus formed.

This process is preferred when it is desired to prepare a compound containing a moiety potentially labile on hydrogenation, such as a nitro or cyano group.

Suitable water soluble complex hydrides include borohydrides such as lithium borohydride, sodium cyanoborohydride, sodium borohydride, potassium borohydride or the like. In general an excess of the hydride is employed.

The reaction is carried out in an aqueous medium, for example in water or in a mixture of water with an inert water miscible organic solvent such as tetrahydrofuran, dioxan or the like.

It is a favoured feature of this invention that ambient and near ambient temperatures may be employed, for example the reaction may be carried out at a temperature of from 0° to 30° and conveniently at ambient, for example at about 18°-25°.

The pH of the reaction is best kept below 10 and this may be effected by the addition of an acid such as hydrochloric or like mineral acid, or by the addition of a suitable sulphonic acid ion-exchange resin for example Amberlite ® IR-120, simultaneously with the complex hydride. This may be carried out in a pH-stat or other similar system.

Once the reaction is over it is advantageous to return the pH to about 5–8.

The desired product may be obtained from the reaction mixture by evaporation of the solvent. Purification may be effected by crystallisation (for example before all the solvent has been evaporated off) or by column chromatography, for example using silica gel or cellulose and butanol/ethanol/water 4/4/1.

The compounds of the formula (VIII) are novel and as such form an aspect of this invention.

The present invention also provides a process for the preparation of a compound of the formula (VIII) which process comprises the reaction of 9-aminodeoxyclavulanic acid with a compound of the formula (IX):

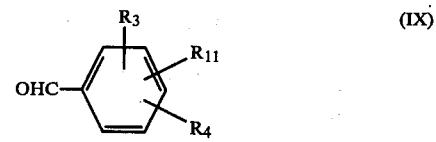

wherein $R_3$, $R_4$ and $R_{11}$ are as defined in relation to formula (VIII) in an aqueous solvent wherein the solution is maintained at an alkaline pH.

The pH of the solution is most suitably maintained in the region of 7–10 and preferably 8–9. This may be effected by the addition of base such as an alkali or alkaline earth metal hydroxide, a carbonate or bicarbonate or with a strong organic base which is unreactive towards aldehydes. Thus suitable bases include lithium hydroxide, sodium hydroxide, potassium hydroxide, calcium hydroxide, barium hydroxide, sodium carbonate, potassium bicarbonate, triethylamine and the like. It is convenient to add the base automatically, for example in a pH-stat.

Solvents suitable for use in this process include water and water in a mixture with inert water miscible organic solvents such as tetrahydrofuran, dioxan, dimethylformamide and the like.

The temperature under which this reaction proceeds is convenient in that it is at or near ambient for example 0°–30° C. and more suitably 18°–25° C.

Most suitably an excess of the aldehyde of the formula (IX) is present, for example a 2–10 fold excess.

The compound of the formula (VIII) is generally only stable in the presence of excess aldehyde. For this reason, and for general convenience, it is preferred to form and use the compound of the formula (VIII) in situ. This adds to the commercial attractiveness of this overall process for the preparation of the compounds of the formula (II).

9-Aminodeoxyclavulanic acid, its preparation and its use are described in our co-pending U.S. Ser. No. 900,541, now U.S. Pat. No. 4,258,080.

The following Examples illustrate the invention.

DESCRIPTION 1

Benzyl 9-N-(4'-cyanobenzyl)-N-(2'-methylallyl)aminodeoxyclavulanate

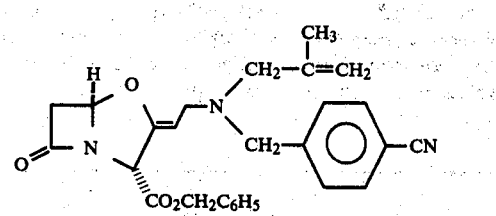

Benzyl 9-O-dichloroacetyl clavulanate (6.50 g; 16.25 mmol) in 'dry' acetonitrile (65 ml) was treated at 0° C. with dropwise addition of N-(4-cyanobenzyl)-N-(2-methylallyl)amine (5.74 g; 31.0 mmol) in 'dry' acetonitrile (60 mls). The reaction mixture was then stirred at between 0° and 20° C. for 6 hours. The solvent was then removed under a reduced pressure and the resulting brown oil dissolved in ethyl acetate (200 ml) The organic mixture was then washed with water (3 × 100 ml), saturated sodium chloride solution and dried (MgSO$_4$). Evaporation to dryness gave a dark yellow oil which on column chromatography afforded the title compound as a colourless oil (12% yield).

$\nu_{max}$ (CHCl$_3$): 2200, 1798, 1738 and 1600 cm$^{-1}$.

$\delta$(CDCl$_3$): 1.70 (3H, s, C(CH$_3$)=CH$_2$), 2.85

(2H, s, N—CH$_2$—$\overset{|}{C}$(CH$_3$)), 3.02 (1H, d, J 17 Hz, 6β-CH), 3.09 (2H, d, J 7 Hz, 9-CH$_2$), 3.40 (1H, dd, J 17 and 3 Hz, 6α-CH), 3.45 (2H, s, N—CH$_2$—⟨⟩—CN), 4.68 (1H, br. t, J 7 Hz, 8-CH), 4.85 (2H, br. s, $\overset{CH_3}{\overset{|}{C}}$=CH$_2$), 5.04 (1H, s, 3-CH), 5.18 (2H, s, CO$_2$CH$_2$), 5.60 (1H, m, 5-CH),
7.40 (9H, m, CH$_2$C$_6$H$_5$ and CH$_2$C$_6$H$_4$CN).

EXAMPLE 1

9-N-(4'-Cyanobenzyl)aminodeoxyclavulanic acid

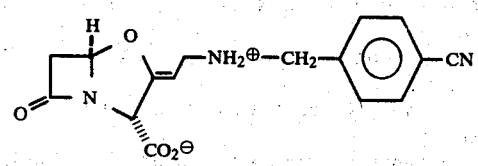

Benzyl 9-N-(4'-cyanobenzyl)-N-(2'-methylallyl)aminodeoxyclavulanate (800 mg, 1.75 mmol) in 'dry' tetrahydrofuran (2 mls) was added carefully to a prehydrogenated mixture of 10% palladium on charcoal (300 mg) in ethanol (30 ml). The mixture was then hydrogenated at atmospheric pressure for 20 minutes. The catalyst was then filtered off under nitrogen and the "pad" was washed well with aqueous ethanol. The filtrate plus washings were then evaporated to dryness to give a brown gum. This gum was chromatographed on silica-gel eluting with tetrahydrofuran-ethanol:water 30:1:1 grading to 5:1:1 affording the title compound as a white solid in 10% yield.

$\nu_{max}$ (KBr): 2225, 1785, 1690 and 1615 cm$^{-1}$.

$\delta$(D$_2$O): 3.12 (1H, d, J 17 Hz, 6β—CH), 3.64 (1H, dd, J 17 and 3 Hz, 6α-CH), 3.80 (2H, d, J 7 Hz, 9—CH$_2$), 4.30 (2H, s, N—CH$_2$—), 4.85 (1H, br. t, J 7 Hz, 8—CH), 5.03 (1H, s, 3—CH), 5.77 (1H, d, J 3 Hz, 5—CH), 7.62

(2H, d, J 7 Hz, 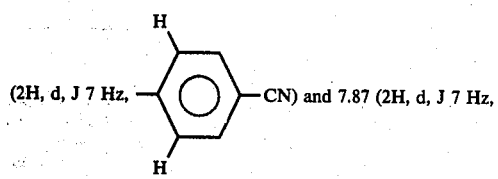—CN) and 7.87 (2H, d, J 7 Hz,

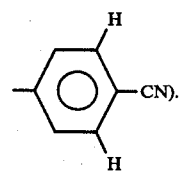—CN).

EXAMPLE 2

9-(4'-Nitrobenzyl)aminodeoxyclavulanic Acid

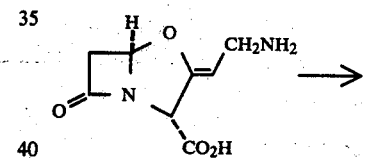

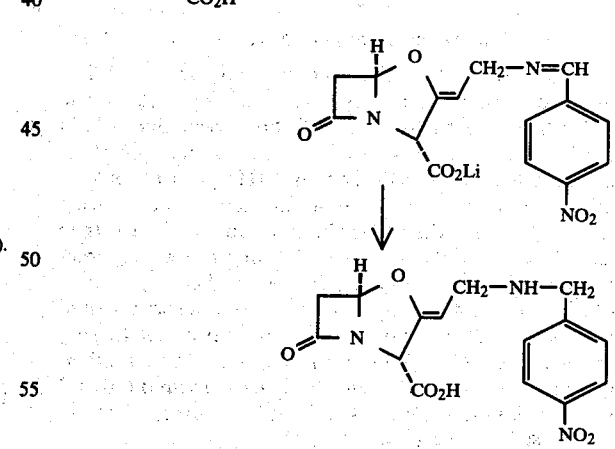

To a stirred solution of 9-aminodeoxyclavulanic acid (0.2 g) in water (10 ml) and tetrahydrofuran (10 ml) was added p-nitrobenzaldehyde (0.8 g). The pH was maintained at 8.5 by the addition of 1 M LiOH solution. When the uptake of LiOH became very slow (93% of theory) the pH was increased to 9.5. At this point the solution contained the Schiffs base. Sodium borohydride (0.2 g) was added in small portions, maintaining the pH of the solution at 9.5–10 by the automatic addition of 1 M HCl solution (3.9 ml). The pH of the solution was adjusted to 7 by the addition of HCl; at this time tlc (Butanol-isopropanol-water 7:7:6) showed that the starting amine had almost disappeared and a new, faster-running zone had appeared. The mixture was evaporated to dryness in vacuo, n-propanol being added to assist in the removal of water and diminish foaming. The residue was extracted with 2×25 ml portions of ethyl acetate, which were decanted off. The insoluble material was treated with water (1.5 ml) and cooled to 2°–5° C. overnight. The crystalline product was filtered off, washed with acetone and then with ether and dried, to yield 9-(4'-nitrobenzyl)aminodeoxyclavulanic acid (50 mgs).

Ir (Nujol mull) 2400–3650 (broad, with fine structure) 1805, 1695, 1615 and 1585 cm$^{-1}$.

EXAMPLE 3

9-(3'-Cyano)benzylaminodeoxyclavulanic acid

To a solution of 9-aminodeoxyclavulanic acid (0.2 g) in water (10 ml) and 3-cyanobenzaldehyde (0.6 g) in redistilled tetrahydrofuran (10 ml) was added 1 M NaOH solution at a rate sufficient to maintain the pH at between 8.0 and 8.5. IR 120 resin (H+ form) was then added simultaneously with sodium cyanoborohydride (0.15 g), keeping the pH at about 8. More resin was then added to reduce the pH to 6.5. The mixture was filtered, evaporated to near dryness in vacuo, then 1-propanol (2ml) added and re-evaporated. The residue was treated with water (3 ml) and the crystalline product filtered off, washed with a little water, acetone and then ether, and dried in vacuo, to yield the title compound (70 mg) $\nu_{max}$ (Nujol mull) 3700–2400 (broad with fine structure) 2218, 1802, 1695 and 1620 cm$^{-1}$.

EXAMPLE 4

9-(4'-Amino)benzylaminodeoxyclavulanic acid

A solution of 9-(4'-nitro)benzylaminodeoxyclavulanic acid (about 20 mg) in water (25 ml) was hydrogenated over 10% palladised charcoal at ambient temperature (~18° C.) and pressure until uptake ceased. The catalyst was filtered off through a bed of kieselguhr and the filtrate evaporated to crystallisation. After trituration with acetone the product was collected by filtration, washed with acetone and dried in vacuo, to yield 11 mg of the desired compound; $\nu_{max}$ (Nujol Mull) 3600–2600 (broad), 1780, 1695 and 1620 cm$^{-1}$.

Nmr $\delta$ (D$_2$O): 3.05 (1H, d, J 17 Hz, 6-$\beta$—CH), 3.55 (1H, dd, J 3 and 17 Hz, 6-$\alpha$—C$\underline{H}$), 3.65 (2H, d, J 8 Hz, 9-C$\underline{H}_2$), 4.05 (2H, s, PhC$\underline{H}_2$) (C3—$\underline{H}$ and C8—$\underline{H}$ obscured by HOD peak), 5.70 (1H, m, 5—C$\underline{H}$), 6.80 and 7.20 (4H, A$_2$B$_2$q., J 8 Hz, C$_6\underline{H}_4$).

DEMONSTRATION OF ACTIVITY

In a standard microtitre technique the minimum inhibitory concentrations (MIC's) of the compounds of this invention alone and together with ampicillin were determined. (Dilution in tryptone soy broth; heavy inoculum.)

| | | Staph. aureus Russell | Kleb. aerogenes E70 | E. coli JT39 |
|---|---|---|---|---|
| Ampicillin alone | | 500–1000 | 500–1000 | ≧2000 |
| Ampicillin + 9-N-(4'-Nitrobenzyl) aminodeoxyclavulanic acid at | 1.0μg/ml | <0.01 | 3.1 | 4.0 |
| | 5.0μg/ml | <0.01 | 1.6 | 1.0 |
| 9-N-(4'-Nitrobenzyl)aminodeoxyclavulanic acid alone | | 2.0 | 62 | 31 |
| Ampicillin + 9-N-(4'-Cyanobenzyl) aminodeoxyclavulanic acid at | 1.0μg/ml | 0.16 | 6.2 | 16 |
| | 5.0μg/ml | <0.01 | 6.2 | 8 |
| 9-N-(4'-Cyanobenzyl)aminodeoxyclavulanic acid alone | | 4.0 | 250 | 62 |
| Ampicillin + 9-N-(4'-Aminobenzyl), aminodeoxyclavulanic acid at | 1.0μg/ml | 0.16 | 25 | 8.0 |
| | 5.0μg/ml | <0.01 | 3.1 | 4.0 |
| 9-N-(4'-Aminobenzyl)aminodeoxyclavulanic acid alone | | 8.0 | >250 | 62.5 |
| Ampicillin + 9-N-(3'Cyanobenzyl) aminodeoxyclavulanic acid at | 1.0μg/ml | 0.08 | 3.1 | 8.0 |
| | 5.0μg/ml | <0.01 | 3.1 | 4.0 |
| 9-N(3'-Cyanobenzyl)aminodeoxyclavulanic acid alone | | 4.0 | 250 | 31.2 |

What we claim is:

1. A compound of the formula (II):

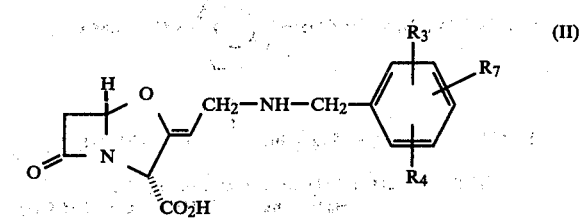

wherein R$_3$ is hydrogen, fluorine, chlorine, alkyl of 1–3 carbon atoms, alkoxyl of 1–3 carbon atoms or alkanoyloxy of 1–3 carbon atoms, R$_4$ is hydrogen, fluorine, chlorine, alkyl of 1–3 carbon atoms or alkoxy of 1–3 carbon atoms, and R$_7$ is nitro, cyano, amino or aminomethyl.

2. A compound according to claim 1 wherein R$_7$ is nitro.

3. A compound according to claim 1 wherein R$_7$ is amino.

4. A compound according to claim 1 wherein R$_7$ is cyano.

5. A compound according to claim 1 wherein R$_7$ is aminoethyl.

6. A compound according to claim 1 wherein R$_3$ is hydrogen, fluorine, chlorine, methoxyl or methyl.

7. A compound according to claim 1 wherein R$_4$ is hydrogen, methyl or methoxyl.

8. A compound according to claim 1 wherein $R_3$ is hydrogen, and $R_4$ is hydrogen.

9. A method of treating bacterial infections in humans or domestic mammals which comprises administering to a human or domestic mammal in need thereof an antibacterially effective amount of a pharmaceutically acceptable acid addition salt of a compound of the formula (IV) or (VI):

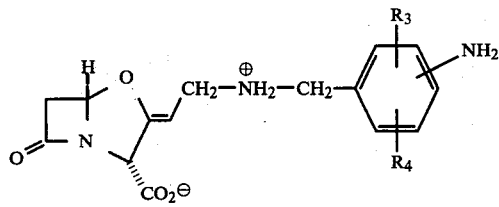

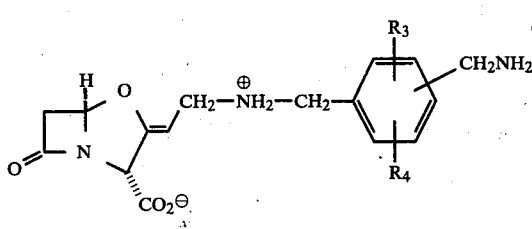

wherein $R_3$ is hydrogen, fluorine, chlorine, alkyl of 1–3 carbon atoms, alkoxyl of 1–3 carbon atoms or alkanoyloxy of 1–3 carbon atoms, and $R_4$ is hydrogen, fluorine, chlorine, alkyl of 1–3 carbon atoms or alkoxy of 1–3 carbon atoms, in combination with a pharmaceutically acceptable carrier.

10. A method of treating bacterial infections in humans and domestic mammals which comprises administering to a human or domestic mammal in need thereof an antibacterially effective amount of a compound of the formula (II):

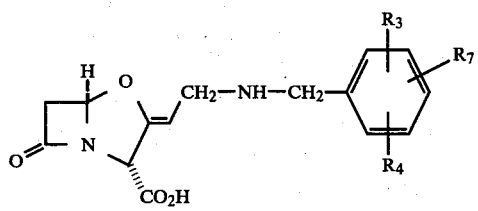

wherein $R_3$ is hydrogen, fluorine, chlorine, alkyl of 1–3 carbon atoms, alkoxyl of 1–3 carbon atoms or alkanoyloxy of 1–3 carbon atoms, $R_4$ is hydrogen, fluorine, chlorine, alkyl of 1–3 carbon atoms or alkoxy of 1–3 carbon atoms, and $R_7$ is nitro, amino or aminomethyl, in combination with a pharmaceutically acceptable carrier.

11. A method according to claim 10 wherein the compound 9-N-(3'-cyanobenzyl) aminodeoxyclavulanic acid.

12. A method according to claim 10 wherein the compound 9-N-(4'-cyanobenzyl) aminodeoxyclavulanic acid.

13. A method according to claim 10 wherein the compound 9-N-(4'-nitrobenzyl) aminodeoxyclavulanic acid.

14. A method according to claim 10 wherein the compound 9-N-(4'-aminobenzyl) aminodeoxyclavulanic acid.

15. A compound according to claim 1 of the formula (III), (IV), (V) or (VI):

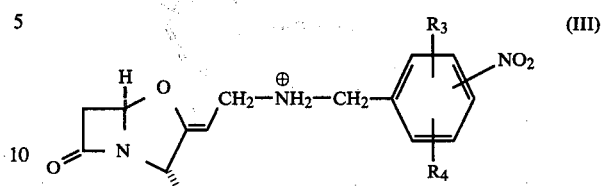

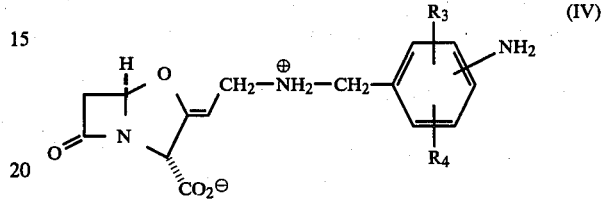

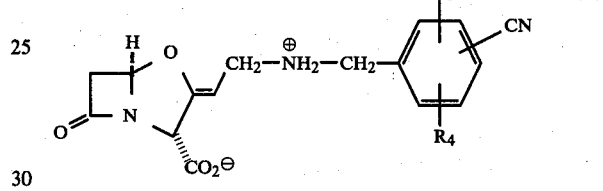

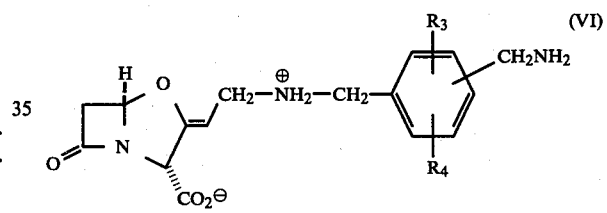

wherein $R_3$ is hydrogen, fluorine, chlorine, alkyl of 1–3 carbon atoms, alkoxyl of 1–3 carbon atoms or alkanoyloxy of 1–3 carbon atoms, and $R_4$ is hydrogen, fluorine, chlorine, alkyl of 1–3 carbon atoms or alkoxy of 1–3 carbon atoms.

16. A compound according to claim 15 wherein $R_3$ is hydrogen, chlorine, fluorine, methoxyl, ethoxyl, acetoxyl, propionoxyl, methyl or ethyl.

17. A compound according to claim 15 wherein $R_4$ is hydrogen, fluorine, chlorine, methoxyl, ethoxyl, acetoxyl, propionoxyl, methyl or ethyl.

18. A compound according to claim 15 wherein $R_3$ and $R_4$ are each hydrogen.

19. A pharmaceutically acceptable addition salt of a compound of the formula (IV) or (VI):

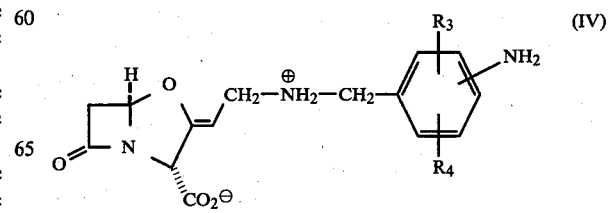

-continued

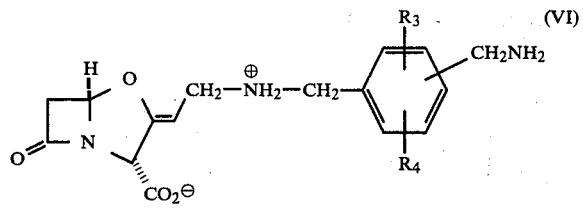

wherein $R_3$ is hydrogen, fluorine, chlorine, alkyl of 1–3 carbon atoms, alkoxyl of 1–3 carbon atoms or alkanoyloxy of 1–3 carbon atoms, and $R_4$ is hydrogen, fluorine, chlorine, alkyl of 1–3 carbon atoms or alkoxy of 1–3 carbon atoms.

20. A salt according to claim 19 which is the hydrochloride salt.

21. The compound according to claim 1 which is 9-N-(3'-cyanobenzyl)aminodeoxyclavulanic acid.

22. The compound according to claim 1 which is 9-N-(4'-cyanobenzyl)aminodeoxyclavulanic acid.

23. The compound according to claim 1 which is 9-N-(4'-nitrobenzyl)aminodeoxyclavulanic acid.

24. The compound according to claim 1 which is 9-N-(4'-aminobenzyl)aminodeoxyclavulanic acid.

25. A pharmaceutical composition useful for treating bacterial infections in humans or domestic mammals which comprises an antibacterially effective amount of a compound of the formula (II):

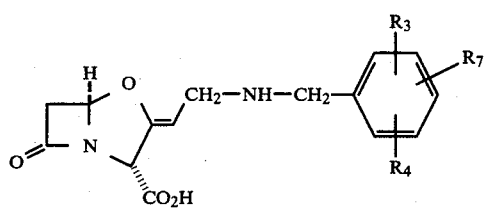

wherein $R_3$ is hydrogen, fluorine, chlorine, alkyl of 1–3 carbon atoms, alkoxyl of 1–3 carbon atoms or alkanoyloxy of 1–3 carbon atoms, $R_4$ is hydrogen, fluorine, chlorine, alkyl of 1–3 carbon atoms or alkoxy of 1–3 carbon atoms, and $R_7$ is nitro, amino or aminomethyl as the sole antibacterial agent, in combination with a pharmaceutically acceptable carrier.

26. A composition according to claim 25 wherein $R_7$ is nitro.

27. A composition according to claim 25 wherein $R_7$ is amino.

28. A composition according to claim 25 wherein $R_7$ is cyano.

29. A composition according to claim 25 wherein $R_7$ is aminoethyl.

30. A composition according to claim 25 wherein $R_3$ is hydrogen, fluorine, chlorine, methoxyl or methyl.

31. A composition according to claim 25 wherein $R_4$ is hydrogen, methyl or methoxyl.

32. A composition according to claim 25 wherein $R_3$ is hydrogen and $R_4$ is hydrogen.

33. A composition according to claim 25 wherein the compound is of the formula (III), (IV), (V) or (VI):

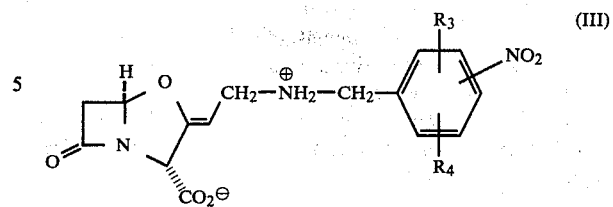

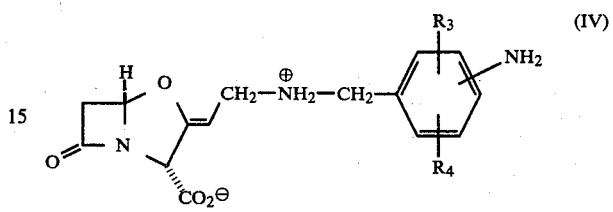

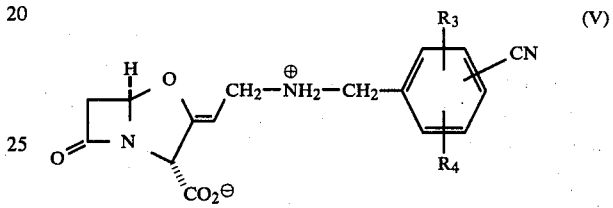

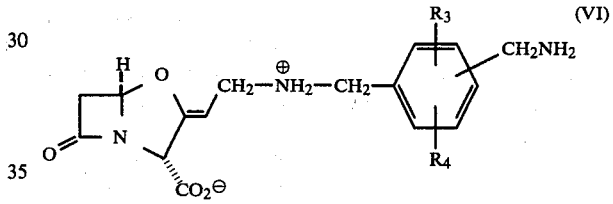

wherein $R_3$ is hydrogen, fluorine, chlorine, alkyl of 1–3 carbon atoms, alkoxyl of 1–3 carbon atoms or alkanoyloxy of 1–3 carbon atoms, and $R_4$ is hydrogen, fluorine, chlorine, alkyl of 1–3 carbon atoms or alkoxy of 1–3 carbon atoms.

34. A composition according to claim 25 wherein $R_3$ is hydrogen, chlorine, fluorine, methoxyl, ethoxyl, acetoxyl, propianoxyl, methyl or ethyl.

35. A composition according to claim 25 wherein $R_4$ is hydrogen, fluorine, chlorine, methoxyl, ethyoxyl, acetoxyl, propianoxyl, methyl or ethyl.

36. A composition according to claim 25 wherein $R_3$ and $R_4$ are each hydrogen.

37. A pharmaceutical composition useful for treating bacterial infections in humans and domestic mammals which comprises an antibacterially effective amount of a pharmaceutically acceptable acid addition salt of a compound of the formula (IV) or (VI):

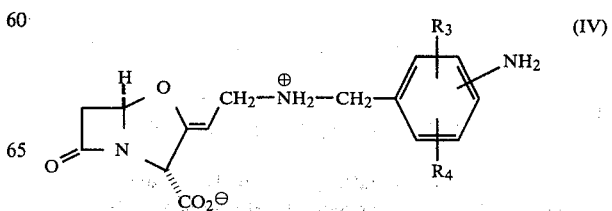

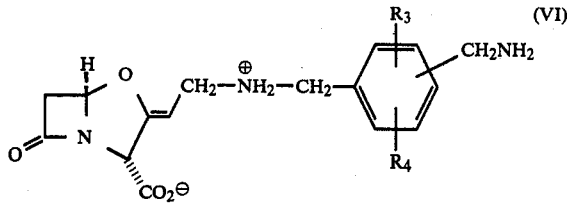

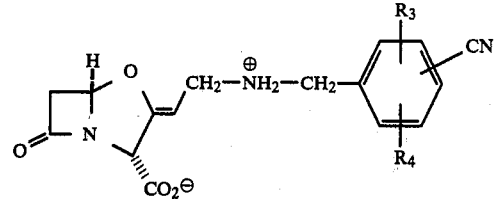

carbon atoms or alkoxy of 1-3 carbon atoms as the sole antibacterial agent, in combination with a pharmaceutically acceptable carrier.

38. A composition according to claim 37 wherein the salt is the hydrochloride salt.

39. A composition according to claim 25 in oral administration form.

40. A composition according to claim 25 in parenteral administration form.

41. A composition according to claim 25 in injectible administration form.

42. A composition according to claim 25 in infusion administration form.

43. A composition according to claim 25 in a form suitable for topical administration.

44. A composition according to claim 25 wherein the compound 9-N-(4'-aminobenzyl) aminodeoxyclavulanic acid.

45. A method according to claim 10 wherein $R_7$ is nitro.

46. A method according to claim 10 wherein $R_7$ is amino.

47. A method according to claim 10 wherein $R_7$ is cyano.

48. A method according to claim 10 wherein $R_7$ is aminoethyl.

49. A method according to claim 10 wherein $R_3$ is hydrogen, fluorine, chlorine, methoxyl, or methyl.

50. A method according to claim 10 wherein $R_4$ is hydrogen, methyl or methoxyl.

51. A method according to claim 10 wherein $R_3$ is hydrogen and $R_4$ is hydrogen.

52. A method according to claim 10 wherein the compound is of the formula (III), (IV), (V) or (VI):

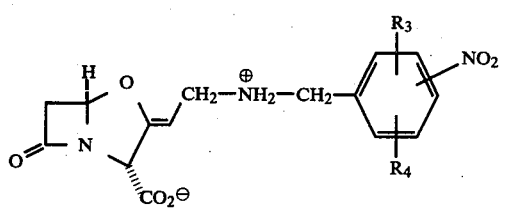

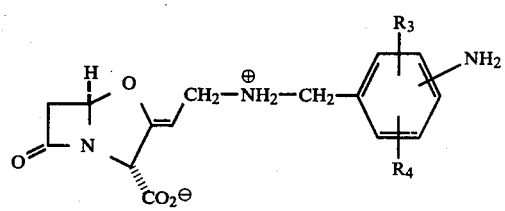

wherein $R_3$ is hydrogen, fluorine, chlorine, alkyl of 1-3 carbon atoms, alkoxyl of 1-3 carbon atoms or alkanoyloxy of 1-3 carbon atoms, and $R_4$ is hydrogen, fluorine, chlorine, alkyl of 1-3 carbon atoms or alkoxy of 1-3 carbon atoms.

53. A method according to claim 10 wherein $R_3$ is hydrogen, chlorine, fluorine, methoxyl, ethoxyl, acetoxyl, propionoxyl, methyl or ethyl.

54. A method according to claim 10 wherein $R_4$ is hydrogen, fluorine, chlorine, methoxy, ethyoxyl, acetoxyl, propionoxyl, methyl or ethyl.

55. A method according to claim 10 wherein $R_3$ and $R_4$ are each hydrogen.

56. A method according to claim 52 wherein $R_7$ is aminomethyl.

57. A method according to claim 10 wherein the salt is the hydrochloride salt.

58. A method according to claim 10 in oral administration form.

59. A method according to claim 10 in parenteral administration form.

60. A method according to claim 10 in injectible administration form.

61. A method according to claim 10 in infusion administration form.

62. A method according to claim 10 in a form suitable for topical administration.

63. A composition according to claim 25 wherein the compound 9-N-(3'-cyanobenzyl) aminodeoxyclavulanic acid.

64. A composition according to claim 25 wherein the compound 9-N-(4'-cyanobenzyl) aminodeoxyclavulanic acid.

65. a composition according to claim 25 wherein the compound 9-N-(4'-nitrobenzyl) aminodexyclavulanic acid.

66. A composition according to claim 33 wherein $R_7$ is nitro.

67. A composition according to claim 33 wherein $R_7$ is amino.

68. A composition according to claim 33 wherein $R_7$ is cyano.

69. A composition according to claim 33 wherein $R_7$ is aminomethyl.

70. A method according to claim 52 wherein $R_7$ is nitro.

71. A method according to claim 52 wherein $R_7$ is amino.

72. A method according to claim 52 wherein $R_7$ is cyano.

73. A compound according to claim 15 wherein $R_7$ is nitro.

74. A compound according to claim 15 wherein $R_7$ is amino.

75. A compound according to claim 15 wherein $R_7$ is cyano.

76. A compound according to claim 15 wherein $R_7$ is aminomethyl.

* * * * *

UNITED STATES PATENT AND TRADEMARK OFFICE
CERTIFICATE OF CORRECTION

PATENT NO. : 4,343,806
DATED : August 10, 1982
INVENTOR(S) : JOHN BARRY HARBRIDGE It is certified that error appears in the above-identified patent and that said Letters Patent are hereby corrected as shown below:

IN THE CLAIMS:

Claim 29, line 2, change "aminoethyl" to --aminomethyl--.

Claim 48, line 2, change "aminoethyl" to --aminomethyl--.

Signed and Sealed this

Thirteenth Day of November 1984

[SEAL]

Attest:

GERALD J. MOSSINGHOFF

Attesting Officer

Commissioner of Patents and Trademarks